(12) United States Patent
Serno et al.

(10) Patent No.: US 8,613,950 B2
(45) Date of Patent: Dec. 24, 2013

(54) PHARMACEUTICAL FORMS WITH IMPROVED PHARMACOKINETIC PROPERTIES

(75) Inventors: Peter Serno, Gladbach (DE); Roland Heinig, Wuppertal (DE); Kerstin Pauli, Dortmund (DE); Yutaka Hayauchi, Leverkusen (DE)

(73) Assignee: Bayer Intellectual Property GmbH, Monheim (DE)

( * ) Notice: Subject to any disclaimer, the term of this patent is extended or adjusted under 35 U.S.C. 154(b) by 1041 days.

(21) Appl. No.: 11/885,019

(22) PCT Filed: Feb. 16, 2006

(86) PCT No.: PCT/EP2006/001393
§ 371 (c)(1), (2), (4) Date: Jun. 9, 2008

(87) PCT Pub. No.: WO2006/092207
PCT Pub. Date: Sep. 8, 2006

(65) Prior Publication Data
US 2008/0249096 A1  Oct. 9, 2008

(30) Foreign Application Priority Data
Mar. 1, 2005 (DE) .......................... 10 2005 009 240

(51) Int. Cl.
*A61K 31/53* (2006.01)
*A61K 9/20* (2006.01)
*A61K 9/00* (2006.01)

(52) U.S. Cl.
CPC ............ *A61K 9/2018* (2013.01); *A61K 9/0056* (2013.01); *A61K 31/53* (2013.01)
USPC .......................................................... 424/489

(58) Field of Classification Search
None
See application file for complete search history.

(56) References Cited

U.S. PATENT DOCUMENTS

| | | | |
|---|---|---|---|
| 2,705,715 A | 4/1955 | Baker et al. | |
| 3,036,070 A | 5/1962 | Druey et al. | |
| 3,169,129 A | 2/1965 | Rodgers et al. | |
| 3,331,840 A | 7/1967 | Fry et al. | |
| 3,333,961 A | 8/1967 | Fry et al. | |
| RE26,565 E | 4/1969 | Rodgers et al. | |
| 3,840,537 A | 10/1974 | Garside et al. | |
| 3,941,785 A | 3/1976 | Clarke et al. | |
| 4,039,544 A | 8/1977 | Broughton et al. | |
| 4,052,390 A | 10/1977 | Broughton et al. | |
| 4,060,615 A | 11/1977 | Matier et al. | |
| 4,159,330 A | 6/1979 | Doria et al. | |
| 4,167,568 A | 9/1979 | Knowles et al. | |
| 4,278,673 A | 7/1981 | Hartley et al. | |
| 4,379,788 A | 4/1983 | Heider et al. | |
| 4,431,440 A | 2/1984 | Bhalla et al. | |
| 4,666,908 A | 5/1987 | Hamilton | |
| 4,885,301 A | 12/1989 | Coates | |
| 4,923,874 A | 5/1990 | McMahon et al. | |
| 5,047,404 A | 9/1991 | Coates et al. | |
| 5,073,559 A | 12/1991 | Coates | |
| 5,075,310 A | 12/1991 | Coates et al. | |
| 5,147,875 A | 9/1992 | Coates et al. | |
| 5,250,534 A | 10/1993 | Bell et al. | |
| 5,254,571 A | 10/1993 | Coates et al. | |
| 5,272,147 A | 12/1993 | Bell et al. | |
| 5,294,612 A | 3/1994 | Bacon et al. | |
| 5,316,906 A | 5/1994 | Haugland et al. | |
| 5,346,901 A | 9/1994 | Bell et al. | |
| 5,426,107 A | 6/1995 | Bell et al. | |
| 5,482,941 A | 1/1996 | Terrett | |
| 5,552,152 A | 9/1996 | Shen | |
| 5,556,847 A | 9/1996 | Johnson et al. | |
| 5,574,020 A | 11/1996 | Klink et al. | |
| 5,591,742 A | 1/1997 | Bell et al. | |
| 5,719,283 A | 2/1998 | Bell et al. | |
| 5,734,053 A | 3/1998 | Terrett | |
| 6,075,028 A | 6/2000 | Graham | |
| 6,100,270 A | 8/2000 | Campbell | |
| 6,143,746 A | 11/2000 | Daugan et al. | |
| 6,221,402 B1 | 4/2001 | Itoh | |
| 6,362,178 B1 | 3/2002 | Niewohner et al. | |
| 6,465,010 B1 * | 10/2002 | Lagoviyer et al. | 424/465 |
| 6,503,908 B1 | 1/2003 | Maw | |
| 6,566,360 B1 | 5/2003 | Niewohner et al. | |
| 6,890,922 B2 | 5/2005 | Niewohner et al. | |
| 6,943,163 B2 | 9/2005 | Niewohner et al. | |
| 6,964,780 B1 | 11/2005 | King et al. | |
| 7,067,149 B1 | 6/2006 | Chauveau et al. | |

(Continued)

FOREIGN PATENT DOCUMENTS

| | | | |
|---|---|---|---|
| CA | 2492747 A1 | 1/2004 | |
| DE | 10232113 | 1/2004 | ............ A61K 31/53 |

(Continued)

OTHER PUBLICATIONS

De Villiers, J. Pharm. Biomed. Anal., 1995, 13(3), pp. 191-198.*

(Continued)

*Primary Examiner* — Brian Gulledge
(74) *Attorney, Agent, or Firm* — Edwards Wildman Palmer LLP; Ralph A. Loren; Nicholas J. DiCeglie, Jr.

(57) ABSTRACT

The present application relates to novel drug formulations of vardenafil which dissolve rapidly in the mouth and lead to increased bioavailability and to a plateau-like plasma concentration profile, and to processes for their preparation.

18 Claims, 1 Drawing Sheet

(56) References Cited

U.S. PATENT DOCUMENTS

| | | |
|---|---|---|
| 7,091,203 B2 | 8/2006 | Niewohner et al. |
| 7,122,540 B2 | 10/2006 | Niewohner et al. |
| 7,314,871 B2 | 1/2008 | Niewohner et al. |
| 7,695,735 B2 | 4/2010 | Chauveau et al. |
| 8,263,126 B2 | 9/2012 | Oury et al. |
| 2002/0002172 A1 | 1/2002 | Bell-Huff |
| 2002/0119195 A1 | 8/2002 | Sen et al. |
| 2002/0128171 A1 | 9/2002 | Watkins et al. |
| 2003/0022894 A1 | 1/2003 | Serno et al. |
| 2003/0134861 A1 | 7/2003 | Doherty |
| 2003/0175346 A1 | 9/2003 | Billotte et al. |
| 2004/0043996 A1 | 3/2004 | Nadkarni |
| 2004/0109890 A1 | 6/2004 | Sugimoto et al. |
| 2004/0115287 A1 | 6/2004 | Chen et al. |
| 2004/0152700 A1 | 8/2004 | Niewohner et al. |
| 2004/0202715 A1 | 10/2004 | Furitsu et al. |
| 2004/0265380 A1 | 12/2004 | Delmas et al. |
| 2005/0019391 A1 | 1/2005 | Gendrot et al. |
| 2006/0078614 A1 | 4/2006 | Venkatesh |
| 2006/0111354 A1* | 5/2006 | Serno et al. ............... 514/243 |
| 2006/0177508 A1 | 8/2006 | Chauveau et al. |
| 2007/0004744 A1 | 1/2007 | Kreisel |
| 2007/0036861 A1 | 2/2007 | Oury et al. |
| 2008/0268046 A1 | 10/2008 | Zuleger et al. |
| 2010/0016323 A1 | 1/2010 | Niewohner et al. |

FOREIGN PATENT DOCUMENTS

| | | | |
|---|---|---|---|
| EP | 0009384 A1 | 4/1980 | |
| EP | 0162715 A2 | 11/1985 | |
| EP | 0201188 A2 | 12/1986 | |
| EP | 0293063 A1 | 11/1988 | |
| EP | 0347146 A2 | 12/1989 | |
| EP | 0349239 A2 | 1/1990 | |
| EP | 0351058 A1 | 1/1990 | |
| EP | 0352960 A2 | 1/1990 | |
| EP | 0371731 A2 | 6/1990 | |
| EP | 0442204 A2 | 8/1991 | |
| EP | 0463756 A1 | 1/1992 | |
| EP | 0526004 A1 | 2/1993 | |
| EP | 0636626 A1 | 2/1995 | |
| EP | 0669324 A1 | 8/1995 | |
| EP | 0702555 A1 | 3/1996 | |
| EP | 0812845 A1 | 12/1997 | |
| EP | 960621 A2 | 12/1999 | |
| EP | 1074258 A2 | 2/2001 | |
| EP | 1097711 A2 | 5/2001 | |
| EP | 1120120 A1 | 8/2001 | |
| EP | 1413294 A1 | 4/2004 | |
| GB | 790762 A | 2/1958 | |
| GB | 1338235 A | 11/1973 | |
| GB | 1584461 A | 2/1981 | |
| WO | WO-93/06104 A1 | 4/1993 | |
| WO | WO-93/07149 A1 | 4/1993 | |
| WO | WO-93/12095 A1 | 6/1993 | |
| WO | WO-93/23017 A1 | 11/1993 | |
| WO | WO-94/00453 A1 | 1/1994 | |
| WO | WO-94/05661 A1 | 3/1994 | |
| WO | WO-94/28902 A1 | 12/1994 | |
| WO | WO-94/29277 A1 | 12/1994 | |
| WO | WO-96/16657 A1 | 6/1996 | |
| WO | WO-97/03675 A1 | 2/1997 | |
| WO | WO-99/24433 A1 | 5/1999 | |
| WO | WO-9924433 A1 | 5/1999 | |
| WO | WO-99/26946 A1 | 6/1999 | |
| WO | WO 00/57857 * | 3/2000 | ............... A61K 9/20 |
| WO | WO-0020033 A1 | 4/2000 | |
| WO | WO 00/24383 A1 | 5/2000 | |
| WO | WO-0027357 A1 | 5/2000 | |
| WO | WO-00/42992 A2 | 7/2000 | |
| WO | WO-0057857 A1 | 10/2000 | |
| WO | WO-01/05386 A2 | 1/2001 | |
| WO | WO-01/17480 A2 | 3/2001 | |
| WO | WO-01/19357 A2 | 3/2001 | |
| WO | WO-01/27101 A2 | 4/2001 | |
| WO | WO-01/47928 A2 | 7/2001 | |
| WO | WO-01/51042 A2 | 7/2001 | |
| WO | WO-01/77110 A1 | 10/2001 | |
| WO | WO-0205820 A1 | 1/2002 | |
| WO | WO-02/09713 A2 | 2/2002 | |
| WO | WO-0247607 A2 | 6/2002 | |
| WO | WO-02/060422 A2 | 8/2002 | |
| WO | WO-02/064593 A1 | 8/2002 | |
| WO | WO-02062315 A1 | 8/2002 | |
| WO | WO-02085336 A1 | 10/2002 | |
| WO | WO-02092057 A1 | 11/2002 | |
| WO | WO-03039520 A1 | 5/2003 | |
| WO | WO-03/051338 A1 | 6/2003 | |
| WO | WO-03051338 A1 | 6/2003 | |
| WO | WO-03/063875 A1 | 8/2003 | |
| WO | WO-03072084 A1 | 9/2003 | |
| WO | WO 2004/006894 * | 1/2004 | |
| WO | WO-2004006894 A1 | 1/2004 | |
| WO | WO-2004/012702 A1 | 2/2004 | |
| WO | WO-2004017976 A1 | 3/2004 | |
| WO | WO-2004/108062 A2 | 12/2004 | |
| WO | WO-2004110411 A2 | 12/2004 | |
| WO | WO-2005037319 A1 | 4/2005 | |
| WO | 2005110419 | 11/2005 | ........... A61K 31/522 |
| WO | WO-2005/105073 A1 | 11/2005 | |
| WO | WO-2005/110419 A1 | 11/2005 | |
| WO | WO-2006047493 A2 | 5/2006 | |
| WO | WO-2006055142 A2 | 5/2006 | |
| WO | WO-2006058250 A2 | 6/2006 | |
| WO | WO-2006/092207 A1 | 9/2006 | |
| WO | WO-2007002125 A1 | 1/2007 | |
| WO | WO-2007029376 A1 | 3/2007 | |

OTHER PUBLICATIONS

Uekama et al., "Design and In Vitro Evaluation of Slow-Release Dosage Form of Pirentanide: Utility of β-Cyclodextrin," J. Pharm. Sc., vol. 78, No. 3, pp. 244-248, Mar. 1990.

Ammar et al., "Improvement of some pharmaceutical properties of drugs by cyclodextrin complexation," Pharmazie, vol. 51 (1996), pp. 42-51.

Stella et al., "Cyclodextrins: Their Future in Drug Formulation and Delivery," Pharma. Res. 1997, 14, 556-567.

Mura et al., "Improvement of Clonazepan Release from a Carbopol Hydrogel," Pharma. Acta Helv, 1992, 67, 282-288.

Chino et al. "Sustained-Release of Drugs from Cyclodextrin-Containing Hydrogels," Proceed. Intern. Symp. Control. Rel. Bioact. Mater., vol. 19 (1992), pp. 98-99.

Gionchedi et al., "Modification of the Dissolution Behaviour of a Water-insoluble Drug, Naftazone, for Zero-order Release Matrix Preparation," J. Pharm. Pharmacol. vol. 46 (1994), pp. 476-480.

Otero-Espinar et al., "Oral bioavailability of naproxen-β-cyclodextrin inclusion compound," International Journal of Pharmaceutics, 75 (1991), pp. 37-44.

Bischoff et al., "The Oral Efficacy of Vardenafil Hydrochloride for Inducing Penile Erection in a Conscious Rabbit Model," J. Urology, vol. 165, 1316-1318, Apr. 2001.

Abstract XP-002382234 Gefunden im Internet, Quick-Dissolving Tablets Made Easy with Pharmaburst, Special Delivery, SPI Pharma, pp. 1-4 (2002).

Young, J.M., Vardenafil, Expert Opin. on Invest. Drugs, vol. 11(10): 1487-1496 (Oct. 2002).

Dobetti, "Fast-Melting Tablets: Developments and Technologies", Pharma. Tech. Int.,12(9): 32-42 (2000).

H. S. Ahn et al.: "Calcium-Calmodulin-Stimulated and Cyclic-GMP-Specific Phosphodiesterases," Advances in Second Messenger and Phosphoprotein Research, 25: pp. 271-284 (1992).

K-E. Andersson et al.: "Future Drugs for the Treatment of Benign Prostatic Hyperplasia," World J. Urol, vol. 19, 2002, pp. 436-442.

W. J. Aronson et al.: "The Role of Nitric Oxide and Cyclic GMP in Mediating Pelvic Nerve Stimulation Induced Erection in Dogs," J. Urology, 147: 454A (1992).

K. M. Azadzoi et al.: "Diabetes Mellitus Impairs Neurogenic and Endothelium-Dependent Relaxation of Rabbit Corpus Cavernosum Smooth Muscle," J. Urol. 148: 1587-1591 (Nov. 1992).

(56) References Cited

OTHER PUBLICATIONS

K. M. Azadzoi et al.: "Endothelium-Derived Nitric Oxie and Cyclooxygenase Products Modulate Corpus Cavernosum Smooth Muscle Tone," J. Urol. 147: 220-225 (Jan. 1992).
K. M. Azadzoi et al.: "Hypercholesterolemia Impairs Endothelium-Dependent Relaxation of Rabbit Corpus Cavernosum Smooth Muscle," J. Urol., 146: 238-240 (Jul. 1991).
Baratti et al. "Effects of sildenafil on long-term retention of an inhibitory avoidance response in mice." Behavioral Pharmacology, 10:8, pp. 731-737 (1999).
C. Bardelle et al.: "Phosphodiesterase 4 Conformers: Preparation of Recombinant Enzymes and Assay for Inhibitors," Analytical Biochemistry, vol. 275, 1999, pp. 148-155.
J. A. Beavo: "Cyclic Nucleotide Phosphodiesterases: Functional Implications of Multiple Isoforms," Physiological Reviews, 75(4): 725-748 (Oct. 1995).
J. A. Beavo et al.: "Multiple Cyclic Nucleotide Phosphodiesterase," Mol. Pharmacol., 46: 399-405 (1994).
J. A. Beavo et al.: "Primary Sequence of Cyclic Nucleotide Phosphodiestearse Isozymes and the Design of Selective Inhibitors," TIPS, 11: 150-155 (Apr. 1990).
E. Bredberg et al., "Pharmacokinetics of Levodopa and Carbidopa in Rats Following Different Routes of Administration," Pharmaceutical Research, vol. 11, No. 4, 1994, pp. 549-555.
A. Burger: "Relation of Chemical Structure and Biological Activity," Med. Chem., 2nd Ed., Interscience Publishers, inc., New York, pp. 36-45, (1960).
P. A. Bush et al.: "Biosynthesis of Nitric Oxide and Citrulline from L-Arginine by Constitutive Nitric Oxide Synthase Present in Rabbit Corpus Cavernosum," Biochem & BioBiophys. Res. Comm., 186(1): 308-314 (Jul. 1992).
P. A. Bush et al.: "Comparison of Nonadrenergic, Noncholingergic- and Nitric Oxide-Mediated Relaxation of Corpus Cavernosum," Int. J. Impotence Res., 4: 85-93 (1992).
P. A. Bush et al.: "Nitric Oxide is a potent Relaxant of Human and Rabbit Corpus Cavernosum," J. Urology, 147: 1650-1655 (Jun. 1992).
M. A. Bush, : "The Role of the L-Arginine-Nitric Oxide-Cyclic GMP Pathway in Relaxation of Corpus Cavernosum Smooth Muscle," PhD Thesis, University of California, Los Angeles (1993).
DJ.Carbone Jr. et al.: "Medical Therapy for Benign Prostatic Hyperplasia: Sexual Dysfunction and Impact on Quality of Life," International Journal of Impotence Research, No. 15, 2003, pp. 299-306.
I. Charles et al.: "Bicyclic Heterocycles with Nitrogen at the Ring Junction. Part 2. Application of the Dakin-West Reaction to the Synthesis of Imidazo-[5,1-f]-1,2,4-triazin-4(3H)-ones," J. Chem. Soc., Perkin Transactions 1, No. 5, pp. 1139-1146 (May 1980).
Coste et al. "Characterization of a Novel Potent and Specific Inhibitor of Type V Phosphodiesterase." Biochemical Pharmacology 50(10) 1577-1585 (1995).
Dale et al. Organic Process Research & Development 4,17-22 (2000).
F. Desgrandchamps: "Clinical Relevance of Growth Factor Antagonists in the Treatment of Benign Prostatic Hyperplasia," European Urology, 1997; 32 (supp. 1), pp. 28-31.
W. Draber and T. Fujita eds, Rational Approaches to Structure, Activity, and Ecotoxicology of Agrochemicals, CRC Press, Boca Ration, p. 4 (1992).
P. Drescher et al.: "Smooth Muscle Contractility in Prostatic Hyperplasia: Role of Cyclic Adenosine Monophosphate," The Prostate, vol. 25, 1994, pp. 76-80.
Encyclopedia of Organic Reagents for Organic Synthesis, Bromine, and Iodine, John Wiley (2003).
J.J. Gillespie: "Phosphodiesterase-linked Inhibition of Nonmicturition Activity in the Isolated Bladder," BJU International, vol. 93, 2004, pp. 1325-1332.
Goodman and Gilman's, The Pharmacological Basis of Therapeutics, Ed. Gilman, et al., McGraw Hill, 8th Ed., (1990), pp. 33-43.

M. Gopalakrishnan et al.: "Potassium Channel Subtypes as Molecular Targets for Overactive Bladder and other Urological Disorders," Expert Opinon Ther. Targets, vol. 8, No. 5, 2004, pp. 437-458.
H. A. Guess: "Epidemiology and Natural History of Benign Prostatic Hyperplasia," Urologic Clinics of North America, vol. 22, No. 2, May 1995, pp. 247-261.
R. S. Hansen et al.: "Purification fo Two Calcium/Calmodulin-Dependent Forms of Cyclic Nucleotide Phosphodiesterase by Using Conformation-Specific Monoclonal Antibody Chromatography," Proc. Natl. Acad. Sci., vol. 19, May 1982, pp. 2788-2792.
C. A. Heid et al.: "Real Time Quantitative PCR," Genome Research, vol. 6, 1996, pp. 986-994.
Y. Jun et al.: "The Positive Effect of Sildenafil on LUTS from BPH While Treating ED," National Journal of Andrology, vol. 10, No. 9, Sep. 2004, 681-683.
Katz et al.: J. Am. Coll. Cardiol., 36(3): 845-851 (2000).
Knaggs et al. Sulfonation, Kirk-Othmer Encyclopedia of Chemical Technology, 1-13 (2000).
K. Korolkovas, Essentials of Medicinal Chemistry, 2nd Edition, John Wiley & Sons, New York, pp. 78-82 (1988).
Loma "Preliminary report: use of sildenafil to treat dyskinesias in patients with Parkinson's disease." Neurology, vol. 54, No. 7, supp. 3, pp. A90-A91 (2000).
C-S. Lin et al.: "Phosphodiesterases as Therapeutic Targets," Urology, vol. 61, 2003, pp. 685-691.
F. Montorsi et al.: "Review of Phosphodiesterases in the Urogenital System: New Directions for Therapeutic Intervention," J. Sex Med., vol. 1, 2004, pp. 322-336.
F. Sciarra et al.: "Role of Estrogens in Human Benign Prostatic Hyperplasia," Arch. Androl. 2000, vol. 44, No. 3, pp. 213-220.
S. H. Soderling et al.: "Regulation of cAMP and cGMP Signaling: New Phosphodiesterases and New Functions," Current Opinion in Cell Biology, Nov. 12, 2000, pp. 174-179.
D. Spina: "Phosphodiesterase-4 Inhibitors in the Treatment of Inflammatory Lung Disease," Drugs, vol. 63, No. 23, 2003, pp. 2575-2594.
S. Uckert et al.: "Characterization and Functional Relevance of Cyclic Nucleotide Phosphodiesterase Isoenzymes of the Human Prostate," The Journal of Urology, vol. 166, Dec. 2001, pp. 2484-2490.
A. Bowman et al.: "Cyclic GMP Mediates Neurogenic Relaxation in the Bovine Retractor Penis Muscle," Br. J. Pharmac., 81: 665-674 (1984).
B. Dumaitre et al.: "Synthesis and Cyclic GMP Phosphodiesterase Inhibitory Activity of a Series of 6-Phenylpyrazolo[3,4-d]pyrimidones," J. Med. Chem., 39: 1635-1644 (1996).
A. Gibson: "Phosphodiesterase 5 Inhibitors and Nitregic Transmission—From Zaprinast to Sildenafil," Eur. J. Pharmacol., 411: 1-10 (2001).
Giuliano et al. "Comparative Study of the Facilitator Proerectile Effect of Vardenafil and Sildenafil in Anaesthetised Rats." European Urology, supp. 5, No. 39, p. 108.
H. W. Hamilton et al.: "Synthesis and Structure-Activity Relationship of Pyrazolo[4,3-d]pyrimidin-7-ones as Adenosine Receptor Antagonists," J. Med. Chem., 30: 91-96 (1987).
F. Holmquist et al.: "Actions of 3-Morpholinosydnonimin (SIN-1) on Rabbit Isolated Penile Erectile Tissue," J. Urology, 150:1310-1315 (Oct. 1993).
F. Holmquist et al.: "Effects of the Nitric Oxide Synthase Inhibitor Nc—Nitro-L-Arginine on the Erectile Response to Cavernosum Nerve Stimulation in the Rabbit," Acta Physiol. Scand., 143: 299-304 (1991).
L. J. Ignarro et al.: "Neurotransmitter Identity Doubt," Nature, 347: 131 (Sep. 1990).
L. J. Ignarro et al.: "Nitric Oxide and Cyclic GMP Formation upon Electrical Field Stimulation Cause Relaxation of Corpus Cavernosum Smooth Muscle," Biochem & Biophys. Res. Comm., 170(2): 843-850 (Jul. 1990).
N. Kim et al.: "Oxygen Tension Regulates the Nitric Oxide Pathway Physiological Role in Penile Erection," J. Clin. Invest., 91: 437-442 (Feb. 1993).

(56) References Cited

OTHER PUBLICATIONS

N. Kim et al.: "A Nitric Oxide-like Factor Mediates Nonadrenergic-Noncholinergic Neurogenic Relaxation of Penile Corpus Cavernosum Smooth Muscle," J. Clin. Inv., 88: 112-118 (Jul. 1991).
S. G. Korenman et al.: "Treatment of Vasculogenic Sexual Dysfunction with Pentoxifylline," JAGS, 41(d): 363-366 (Apr. 1993).
M. Kozizumi et al.: "4(3H)-Quinazolines," Chugai Pharmaceutical Co., Ltd., Japan, Kokai, JP 52051378, Chem. Abstr. 87: 20171g (1977).
S. J. Lee et al.: "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities," J. Med. Chem., 38: 3547-3557 (1995).
R. T. Morrison and R. N. Boyd: Organic Chemistry, Allyn and Bacon, Inc., 3rd Ed., 1972), pp. 858-859.
K. J. Murray: "Phosphodiesterase VA Inhibitors," 6(3): 150-156 (Apr. 1993).
C. D. Nicholson et al.: "Differential Modulation of Tissue Function and Therapeutic Potential of Selective inhibitors of Cyclic Nucleotide Phosphodiesterase Isoenzymes," TIPS, 12: 19-27 (Jan. 1991).
J. Prickaerts et al., "Possible Role of Nitric Oxide-Cyclic GMP Pathway in Object Recognition Memory: Effect of 7-Nitroindazole and Zaprinast," European Journal of Pharmacology, 37 (1997), pp. 125-136.
J. Rajfer et al.: "Nitric Oxide as a Mediator of Relaxation of the Corpus Cavernosum in Response to Nonadrenergic, Noncholinergic Neurotransmission," The New England Journal of Medicine, 326(2): 90-94 (Jan. 1992).
Rosen & McKenna, PDE-5 Inhibition and Sexual Response; Pharmacological Mechanisms and Clinical Outcomes, Annu. Rev. Sex. Res., 13; 36-88 (2002).
I. Saenz de Tejada et al.: "Cholinergic Neurotransmission in Human Corpus Cavernosum. I. Responses of Isolated Tissue," Am. J. Physiol., 254: H459-H467.
I. Saenz de Tejada et al.: "Impaired Neurogenic and Endothelium-Mediated Relaxation of Penile Smooth Muscle from Diabetic Men with Impotence," N. Engl. Med., 320: 1025-1030 (Apr. 1989).
Schultheiss et al. "Cognitive Side Effects of Sildenafil: An Assessment Using Event-Related Brain Potentials." European Urology 37:2, p. 82 (2000).
P. J. Silver et al.: "Cyclic GMP Potentiation by WIN 58237, a Novel Cyclic Nucleotide Phosphodiesterase Inhibitor," Journal of Pharmacology and Experimental Therapeutics, 271(3): 1143-1149 (1994).
C. G. Stief et al.: "Cyclic Nucleotide Phosphodiesterase (PDE) Isoenzymes in Human Cavernous Smooth Muscle: Characterization and Functional Effects of PDE-Inhibitors in Vitro and In Vivo," Int. J. Impot. Res. 7(1): 03 (Sep. 1995).
E. J. Sybertz et al.; "cGMP Phosphodiesterase Inhibition: A New Mechanism for the Discovery of Therapeutics Agents," Current Pharma. Design. 1(4): 373-390 (1995).
Sybertz et al. "Inhibitors of PDE1 and PDE5 cGMP phospodiesterases: patents and therapeutic potential," Expert Opinion on Therapeutic Patents, Ashley Publications, vol. 7, No. 6, pp. 631-639 (1997).
A. Taher et al.: "Cyclic Nucleotide Phosphodiesterase in human Cavernous Smooth Muscle," World J. Urol., 15: 32-35 (1997).
A. Taher et al.: "Phosphodiesterase Activity in Human Cavernous Tissue and the Effect of Various Selective Inhibitors," J. Urology, 149(4): 285 (Apr. 1993).
A. Taher et al.: "Cyclic Nucleotide Phosphodiesterase Activity in Human Cavernous Smooth Nuscle and the Effect of Various Selective Inhibitors," Int. J. Impotence Res., 4(2): 11 (1992).
Y. Takase et al.: "The Quinazole Derivatives as Novel Potent and Selective Inhibitors of Cyclic GMP-Phosphodiesterase," 206th American Chemical Society National Meeting, Chicago, Il. (1993).
Terret et al. "Sildenafil (Viagra™), a Potent and Selective Inhibitor of Type 5 CGMP Phosphodiesterase with Utility for the Treatment of Male Erectile Dysfunction." Biorg. & Med. Chem. Letters, 6(15) 1819-1824 (1996).
W. J. Thompson: "Cyclic Nucleotide Phosphodiesterases: Pharmacology, Biochemistry and Functions," Pharmac. Ther., 5: 13-33 (1991).
T. J. Torphy et al.: "Characterization and Selective Inhibition of Cyclic Nucleotide Phosphodiesterase Isozymes in Canine Tracheal Smooth Muscle," Molecular Pharmacology, 37: 206-214 (1989).
A. J. Trapani et al.: "Hemodynamic Basis for the Depressor Activity of Zaprinast, a Selective Cyclic GMP Phosphodiesterase Inhibitor," J. Pharmacol. & Exp. Ther., 258: 269-274 (1991).
F. Trigo-Rocha et al.: "The Effect of Intracavernous Injection of Potassium Channel Openers in Monkeys and Dogs," Int. J. Impotence Res., 7: 41-48 (1995).
F. Trigo-Rocha et al.: "The Role of Cyclic Adenosine Monophosphate, Cyclic Guanosine Monophosphate, Endothelium and Nonadrenergic, Noncholinergic Neurotransmission in Canine Penile Erection," J. urology, 149: 872-887 (Apr. 1993).
F. Trigo-Rocha et al.: "Nitric Oxide and cGMP: Mediators of Pelvic Nerve-Stimulated Erection in Dogs," J. Am. Phys., 264(2): H419-H422 (Feb. 1993).
F. Trigo-Rocha et al.: "Intracellular Mechanism of Penile Erection in Monkeys," Neurology and Urodynamics, 13: 71-80 (1994).
Notice of Opposition issued in European Patent No. EP 1858490, by Generics [UK] Limited, dated Jan. 11, 2013.
Notice of Opposition issued in European Patent No. EP 1858490, by Accord Healthcare, dated Jan. 11, 2013.
Fu et al., "Orally fast disintegrating tablets", Critical Reviews in Therapeutic Drug Carrier systems, 21(6); 433-475 (2004).
Compositions of Pharmaburst® B1, B2 and C1, published Apr. 20, 2004.
Pharmeuropa vol. 16, No. 2, Apr. 2004—p. 252—Definitions and Tests of Various Tablets.

* cited by examiner

Mean plasma concentration profile after administration of 10 mg of vardenafil in a preparation according to the invention according to Example 6 (black triangles) and as standard tablet (open circles)
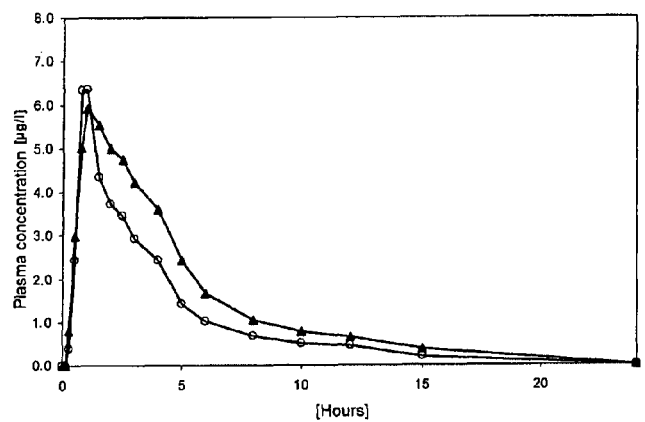

PHARMACEUTICAL FORMS WITH IMPROVED PHARMACOKINETIC PROPERTIES

RELATED APPLICATIONS/PATENTS

This application is a National Stage Application of International Application Number PCT/EP2006/001393, filed on Feb. 16, 2006, which claims priority to German Patent Application Number 102005009240.3, filed on Mar. 1, 2005, the contents each of which are incorporated herein by reference.

The present application relates to novel drug formulations of vardenafil which disintegrate rapidly in the mouth and lead to increased bioavailability and to a plateau-like plasma concentration profile, and to processes for their preparation.

The imidazotriazinone derivate vardenafil and its use as cGMP phosphodiesterase inhibitor and its activity spectrum are known (for example WO 99/24433), and the compound is commercially available under the name Levitra®. However, the therapeutic use of vardenafil is negatively affected by its low bioavailability of about 14% and the rapid decrease in the plasma concentration about 1 hour after the administration of vardenafil. In principle, low bioavailability results in a high variability of the plasma concentrations between different individuals; furthermore, the dosage has to be increased to achieve a particular exposition. The rapid decrease of the plasma concentration about 1 hour after oral administration of vardenafil is associated with the risk of a subsequent reduced therapeutic activity. Accordingly, the patients have to time the administration carefully in order to benefit from high plasma concentrations.

For these reasons, there have been attempts to provide a drug formulation of vardenafil which solves one of the problems mentioned. The Application US 2003/0134861 A1 describes formulations for transmucosal administration of phosphodiesterase inhibitors, for example buccal drug forms or sublingual tablets. However, as is evident from Comparative Examples 1 to 3, in the case of vardenafil administration via the oral mucosa, highly unsatisfactory plasma concentrations with a highly variable, incomplete and slow adsorption of the active compound result.

In addition, drug formulations having a delayed release of cGMP phosphodiesterase inhibitors have been described (WO 00/24383). Such drug formulations can solve the problem of the rapid decrease in the plasma concentrations. However, delayed-release drug formulations are large and, for some of the patients, difficult to swallow. Furthermore, they do not address at all the problem of the low bioavailability of vardenafil.

Furthermore, drug formulations of cGMP phopshodiesterase inhibitors which disintegrate in the mouth have been described. U.S. Pat. No. 6,221,402 describes a drug formulation inter alia for active compounds for impotence in which the active compound-containing core is coated inter alia with a polymer insoluble in saliva. US 2002/0002172 describes a drug formulation of the cGMP phosphodiesterase inhibitor sildenafil which disintegrates in the mouth and which contains the active compound as a poorly water-soluble free base. Such drug formulations which disintegrate in the mouth have the advantage of being easy to take by the patient since the drug formulation already disintegrates in the mouth. However, they neither increase bioavailability nor provide longer retention of plasma concentrations. Since the patient swallows the disintegrated drug formulation after a short period of time, as in the case with a conventional tablet for swallowing, the active compound dissolves only in the stomach. Accordingly, in the best case, the resulting bioavailability is similar to that after administration of conventional tablets for swallowing.

Surprisingly, we have now found drug formulations of vardenafil which disintegrate in the mouth and lead to an increased bioavailability and a plateau-like plasma concentration profile. Compared to a customary tablet to be swallowed with water, the formulations according to the invention have considerably higher bioavailability. Here, the more elevated plasma concentrations are reached in particular in the period in which, in the case of the conventional tablet for swallowing, the plasma concentrations are already decreasing again, i.e., for example, in the period from 0 to 5 hours after the maximum plasma concentration was reached. As a result, at the same dose, an improved activity is anticipated for this period. In particular the increase in plasma concentration even several hours after the administration of a particularly rapidly disintegrating and releasing drug formulation is an unexpected discovery, as the expected result of a more rapid dissolution of the active compound would rather have been a more rapid increase and a more rapid decrease of the vardenafil plasma concentrations.

Accordingly, the present invention provides a vardenafil-comprising drug formulation, which is characterized in that the solubility of the form of vardenafil employed in a small amount of aqueous liquid is sufficiently high and the dissolution rate of the formulation disintegrating in the mouth is sufficiently rapid. It has been found that this is ensured when at least 80% of the vardenafil dose in the substance form employed, for example the salt or the mixture with an acid, dissolves at 25° C. in 10 ml of physiological saline and when the release rate from the drug formulation in 900 ml of physiological saline within the first 5 minutes is at least 70% (37° C., USP pedal stirrer apparatus, 50 revolutions per minute).

A further aspect of the invention is the application of an optimized method of administration for the preparations according to the invention. Usually, transmucosal drug formulations are brought into contact with the mucosa as long and as intensively as possible, for example by sticking an active compound-containing film to the mucosa of the mouth. If this is not desired or not possible, tablets are generally swallowed with a little liquid. It has been found that both procedures have a negative effect on the obtainable bioavailability of vardenafil. In contrast, the bioavailability of vardenafil can be increased when the patient places the drug formulation according to the invention into the oral cavity, waits until it has disintegrated in the mouth and subsequently swallows the resulting solution or suspension. Accordingly, the drug formulations according to the invention are packed in a primary packaging, for example a plastic bottle or a blister pack, and provided with a label or an information leaflet in which the administration procedure mentioned is described.

Specifically, to prepare the formulations according to the invention, vardenafil is present in the form of one of its salts with an acid. The salts may be solvent-free or solvent-containing and may be present in a different polymorphic form. Examples are vardenafil hydrochloride trihydrate, vardenafil dimesilate monohydrate or vardenafil monomesilate. However, salts of vardenafil with citric acid, tartaric acid, succinic acid, sulphur acid, acetic acid, adipic acid, gluconic acid, glucuronic acid, glutaminic acid, glutaric acid, glycerophosphoric acid, lactic acid, maleic acid, malic acid, phosphoric acid, lactobionic acid, malonic acid, naphthalenesulphonic acid, naphthalenedisulphonic acid or toluenesulphonic acid are also possible. Alternatively, it is also possible to obtain formulations according to the invention by jointly incorporating vardenafil and acid into a drug formulation. In this case, the corresponding salt is formed during the dissolution process in the mouth. To achieve the dissolution rate according to the invention, it is furthermore advantageous for the vardenafil salt in the drug formulation to be present in ground, amorphous or already dissolved form. The vardenafil or vardenafil salt is preferably added in micronized form, with a mean particle size of less than 20 μm. The content of vardenafil or vardenafil salt in the drug formulation which rapidly disintegrates in the mouth is preferably between 0.8% and 25% (calculated as vardenafil base).

In one of the known processes, the vardenafil salt is converted into a drug formulation which rapidly disintegrates in the mouth. Here, drug formulations which rapidly disintegrate in the mouth are to be understood as meaning drug formulations where the disintegration time (method of the European Pharmacopoeia) is less than 3 minutes, preferably less than 1 minute. To achieve this, the active compound is suitably mixed with sugars, sugar alcohols, disintegrants or other substances which promote disintegration, and also with further auxiliaries, such as surfactants, lubricants, flow regulators, flavourings, colorants or fillers, and compacting the mixture in a tableting machine. Preference is given here to using sugar alcohols, such as mannitol or sorbitol, in particular in a concentration (based on the finished tablet) of from 40% to 99%. Alternatively, the vardenafil salt may be dissolved or suspended in an aqueous solvent together with auxiliaries such as sugars, sugar alcohols, polymers or surfactants, and the solution or suspension is metered into blister wells and subjected to a freeze-drying process. Likewise alternatively, the vardenafil salt may be dissolved or suspended in an organic solvent together with auxiliaries such as film-formers, plasticizers, flavourings and colorants and be processed into a film. Also possible is a solvent-free film preparation using meltable film formulations. After the preparation, the films are cut into pieces corresponding to an individual dose.

COMPARATIVE EXAMPLE 1

Low and slow absorption of vardenafil hydrochloride from a drug formulation for administration via the mucosa of the mouth 30 mg of vardenafil hydrochloride, 54 mg of methyl parahydroxybenzoate, 6 mg of propyl parahydroxybenzoate and 9 g of sucrose are dissolved in about 20 g of water. The pH is adjusted to 3.9 using 20% strength lactic acid solution. Using water, the mixture is then made up to a total of 33.405 g. In each case 11.97 g of this solution (corresponds to 10 mg of vardenafil) are applied sublingually for 15 minutes to 10 volunteers. For comparison, a customary tablet which is to be swallowed with water and comprises the following components: 11.852 mg of vardenafil hydrochloride trihydrate (corresponds to 10 mg of vardenafil), 105.023 mg of microcrystalline cellulose, 6.25 mg of crosslinked polyvinylpyrrolidone, 0.625 mg of colloidal silica, 1.25 mg of magnesium stearate, 2.391 mg of hypromellose, 0.797 mg of Macrogol 400, 0.653 mg of titanium dioxide, 0.133 mg of yellow iron oxide and 0.011 mg of red iron oxide is administered by the cross-over method. The relative bioavailability for the sublingually administered solution obtained in comparison to this standard tablet serving as a reference is only 24.6%.

COMPARATIVE EXAMPLE 2

Low and slow absorption of vardenafil from a drug formulation for administration via the mucosa of the mouth 2 g of vardenafil, 0.1 g of ascorbyl palmitate, 0.5 g of α-tocopherol and 7.8 g of trometamol are dissolved in 250 g of Polysorbat 20, 400 g of 1,2 propylene glycol, 250 g of ethanol 96%, 35.8 g of 1 M hydrochloric acid and 52.6 g of water. 5 ml of this solution (corresponds to 10 mg of vardenafil) are administered to 10 volunteers sublingually for 15 minutes. In the cross-over comparison, the 10 mg vardenafil tablet described in Comparative Example 1, which is swallowed with water, is administered to the volunteers as a reference. The relative bioavailability of the sublingually administered solution is 18.9%.

COMPARATIVE EXAMPLE 3

Low and slow absorption of vardenafil mesilate from a drug formulation for administration via the mucosa of the mouth For in each case 15 minutes, a tablet consisting of 2.39 mg of vardenafil monomesilate, 0.0986 mg of methane sulphonic acid, 20 mg of mannitol, 2 mg of croscarmellose sodium, 25.3 mg of microcrystalline cellulose, 1 mg of magnesium stearate and 0.25 mg of finely divided silica is administered sublingually to 10 volunteers. The disintegration time of the tablet is 4 minutes. In the cross-over comparison, the 10 mg vardenafil tablet described in Comparative Example 1, which is swallowed with water, is administered to the volunteers as a reference. The relative availability of the sublingual tablet, normalized for the dose, is 43.9%.

COMPARATIVE EXAMPLE 4

Lack of increased bioavailability in the case of a non-inventive tablet which rapidly disintegrates in the mouth 11 volunteers each receive a tablet which rapidly disintegrates in the mouth and consists of 10.7 mg of vardenafil dihydrate (corresponds to 10 mg of vardenafil), 0.484 mg of yellow iron oxide, 0.066 mg of red iron oxide, 1.1 mg of apricot flavour, 4.4 mg of aspartam, 6.6 mg of magnesium stearate and 196.65 mg of Pharmaburst® (commercial mixture of auxiliaries from SPI). This tablet, which rapidly disintegrates in the mouth, is non-inventive since, at 25° C., only about 0.1 mg of vardenafil dihydrate (corresponds to about 1% of the administered dose) dissolves in 10 ml of physiological saline, and the solubility criterion of the active compound form employed is thus not met. In the cross-over comparison with the reference tablet listed in Comparative Example 1, the relative bioavailability is 97.3%.

COMPARATIVE EXAMPLE 5

Lack of increased bioavailability in the case of a non-inventive tablet which rapidly disintegrates in the mouth 11 volunteers each receive a tablet which rapidly disintegrates in the mouth and consists of 10.7 mg of vardenafil dihydrate (corresponds to 10 mg of vardenafil), 5 mg of ground succinic acid, 0.484 mg of yellow iron oxide, 0.066 mg of red iron oxide, 1.1 mg of apricot flavour, 4.4 mg of aspartam, 6.6 mg of magnesium stearate and 191.65 mg of Pharmaburst® (commercial mixture of auxiliaries from SPI). This tablet, which rapidly disintegrates in the mouth, is non-inventive since the release of active compound in 900 ml of physiological saline at 37° C. and 50 rotations per minute in the USP pedal stirrer apparatus is only 40% in 5 minutes, and the dissolution rate criterion according to the invention is thus not met. In the cross-over comparison with the reference tablet listed in Comparative Example 1, the relative bioavailability is 101.8%.

EXAMPLE 6

Demonstration of increased bioavailability for an inventive tablet which rapidly disintegrates in the mouth 12 volunteers each receive a tablet which rapidly disintegrates in the mouth and consists of 11.85 mg of vardenafil hydrochloride trihydrate, 0.55 mg of yellow iron oxide, 0.075 mg of red iron oxide, 0.75 mg of apricot flavour, 0.125 mg of neohesperidin dihydrochalcone, 2.50 mg of aspartame, 0.625 mg of finely divided silica, 3.125 mg of magnesium stearate and 105.4 mg of Pharmaburste. At 25° C., about 10.4 mg (corresponds to 8.8 mg of vardenafil) and thus 88% of the dose of the active compound employed dissolve in 10 ml of physiological saline. The active compound release in 900 ml of physiological saline at 37° C. and 50 rotations per minute in the USP pedal stirrer apparatus is 73% in 5 minutes. Thus, the solubility and dissolution rate criteria according to the invention are met. The relative bioavailability, compared to the reference tablet described in Comparative Example 1, is 141%. The corresponding pharmacokinetic parameters and the mean plasma concentration profile are shown in a comparative manner in Table 1 (Appendix) and FIG. 1 (Appendix), respectively.

EXAMPLE 7

Demonstration of increased bioavailability for an inventive tablet which rapidly disintegrates in the mouth 11 volunteers each receive a tablet which disintegrates in the mouth and consists of 5.93 mg of vardenafil hydrochloride trihydrate, 0.352 mg of yellow iron oxide, 0.048 mg of red iron oxide, 0.48 mg of apricot flavour, 0.08 mg of neohesperidin dihydrochalcone, 1.60 mg of aspartame, 0.40 mg of finely divided silica, 2 mg of magnesium stearate and 69.11 mg of Pharmaburst®. At 25° C., 91% of the active compound employed dissolves in 10 ml of physiological saline. The active compound for release in 900 ml of physiological saline at 37° C. and 50 rotations per minute in the USP pedal stirrer apparatus is 78% in 5 minutes. Thus, the solubility and dissolution rate criteria according to the invention are met. For comparison, a customary tablet to be swallowed with water consisting of the following components: 5.926 mg of vardenafil hydrochloride trihydrate (corresponds to 5 mg of vardenafil), 75.419 mg of microcrystalline cellulose, 4.35 mg of crosslinked polyvinylpyrrolidone, 0.435 mg of colloidal silica, 0.87 mg of magnesium stearate, 1.664 mg of hypromellose, 0.555 mg of Macrogol 400, 0.455 mg of titanium dioxide, 0.092 mg of yellow iron oxide and 0.007 mg of red iron oxide is administered in the cross-over method. The relative bioavailability, compared to this reference tablet, is 149.6%. Even up to 12 hours after administration of the tablet according to the invention, the plasma concentrations are higher than those following administration of the standard tablet.

EXAMPLE 8

Demonstration of increased bioavailability for an inventive tablet which rapidly disintegrates in the mouth The following components are mixed in a ploughshare mixer: 697 g of micronized vardenafil hydrochloride trihydrate, 500 g of a colorant premix consisting of 4.4% of yellow iron oxide, 0.6% of red iron oxide and 95% of Pharmaburst®, 30 g of apricot flavour, 5 g of neohesperidin dihydrochalcone, 100 g of aspartame and 3518 g of Pharmaburst®. The powder mixture is mixed in a tumbler with 25 g of finely divided silica and sieved through a 0.5 mm sieve. This mixture is mixed in a tumbler with 125 g of magnesium stearate for 5 minutes. In a tablet press, the finished powder mixture is compacted to round tablets having a mass of 170 mg, a diameter of 8 mm and a fracture strength of about 35 N. For comparison, a customary tablet which is to be swallowed with water and which consists of the following components: 23.705 mg of vardenafil hydrochloride trihydrate (corresponds to 20 mg of vardenafil), 141.797 mg of microcrystalline cellulose, 8.85 mg of crosslinked polyvinylpyrrolidone, 0.885 mg of colloidal silica, 1.77 mg of magnesium stearate, coated with: 3.385 mg of hypromellose, 1.128 mg of Macrogol 400, 0.925 mg of titanium dioxide, 0.188 mg of yellow iron oxide and 0.015 mg of red iron oxide is administered by the cross-over method. The relative bioavailability, compared to this reference tablet, is 128.2%.

EXAMPLE 9

The following components are mixed and then subjected to dry granulation on a roll: 18.96 kg of vardenafil hydrochloride trihydrate, 76.54 kg of microcrystalline cellulose, 20 kg of crospovidone and 80 kg of calcium silicate. The granules are then mixed with: 1 kg of finely divided silica, 0.5 kg of sucralose, 1 kg of pulverulent orange flavour and 2 kg of sieved magnesium stearate. The finished mixture is compacted in a rotary press to give tablets having a diameter of 7 mm and a mass of 125 mg.

EXAMPLE 10

The following components are mixed: 21.4 kg of vardenafil dihydrate, 60 kg of ground succinic acid, 1.1 kg of sucralose and 342.1 kg of Pharmaburst® B2, 13.2 kg of sieved magnesium stearate and 2.2 kg of pulverulent orange flavour. The mixture is compacted to tablets having a diameter of 9 mm and a mass of 220 mg (corresponds to a dose of 10 mg of vardenafil). At 25° C., 10 mg of vardenafil and 30 mg of succinic acid dissolve completely in 10 ml of physiological saline. The dissolution rate of the tablets is 90% in 5 minutes in the USP pedal stirrer apparatus with 900 ml of physiological saline, at 37° C. and 50 rotations per minute.

TABLE 1

Pharmacokinetic parameters of vardenafil

| | | A<br>Tablet according to the inventionwhich rapidly disintegrates in the mouth geo.mean geo. % CV (N = 12) | B<br>Customary tablet to be swallowed with water geo.mean geo. % CV (N = 12) |
|---|---|---|---|
| AUC | [μg * h/L] | 32.2 (32.0) | 22.8 (38.2) |
| $f_{rel}$ (A:B) | [%] | 140.9 (120.2-165.2) | |
| $C_{max}$ | [μg/L] | 7.51 (43.9) | 7.35 (39.5) |
| $t_{max}$ | [h] | 0.875 (0.50-2.50) | 0.75 (0.50-2.00) |
| $t_{1/2}$ | [h] | 4.12 (22.1) | 4.08 (24.0) |

$t_{max}$ as median (minimum-maximum)
$f_{rel}$ as point estimate (90% confidence interval)

The invention claimed is:

1. A drug formulation of vardenafil which disintegrates rapidly in the mouth, comprising:
   an uncoated tablet which disintegrates rapidly in the mouth and which releases the vardenafil in the mouth without swallowing the tablet, said tablet comprising vardenafil hydrochloride trihydrate, and
   at least one sugar alcohol, and wherein at least 80% of the vardenafil hydrochloride trihydrate in the drug formulation dissolves at 25° C. in 10 ml of physiological saline, and further wherein the rate of release of the vardenafil hydrochloride trihydrate from the drug formulation in 900 ml of physiological saline within the first 5 minutes in the USP pedal stirrer apparatus at 50 rotations per minute at 37° C. is at least 70%.

2. The drug formulation according to claim 1, wherein the vardenafil hydrochloride trihydrate is in micronized form with a mean particle size of less than 20 μm.

3. The drug formulation according to claim 1 or claim 2, wherein said sugar alcohol comprises from 40% to 99% of the total formulation.

4. The drug formulation according to claim 1 or 2, wherein said sugar alcohol is selected from the group consisting of sorbitol, mannitol and mixtures thereof.

5. The drug formulation according to claim 4, wherein said sugar alcohol is mannitol.

6. The drug formulation of claim 4, wherein said sugar alcohol is sorbitol.

7. The drug formulation according to claim 4, wherein said vardenafil hydrochloride trihydrate comprises from 0.8% to 25% of the formulation, calculated as vardenafil free base.

8. A drug formulation in the form of an uncoated tablet which disintegrates rapidly in the mouth and releases the drug in the mouth without swallowing the tablet comprising
vardenafil hydrochloride trihydrate, and
at least two sugar alcohols.

9. The drug formulation according to claim 8, wherein said sugar alcohols are a mixture of sorbitol and mannitol.

10. The drug formulation according to claim 8, wherein at least one sugar alcohol is mannitol.

11. The drug formulation of claim 8, wherein at least one sugar alcohol is sorbitol.

12. The drug formulation according to claim 8, wherein said vardenafil hydrochloride trihydrate comprises from 0.8% to 25% of the formulation, calculated as vardenafil free base.

13. The drug formulation according to claim 8, wherein at least 80% of the vardenafil hydrochloride trihydrate in the drug formulation dissolves at 25° C. in 10 ml of physiological saline.

14. The drug formulation according to claim 8, wherein the rate of release of the vardenafil hydrochloride trihydrate from the drug formulation in 900 ml of physiological saline within the first 5 minutes in the USP pedal stirrer apparatus at 50 rotations per minute at 37° C. is at least 70%.

15. The drug formulation according to claim 8, wherein at least 80% of the vardenafil hydrochloride trihydrate in the drug formulation dissolves at 25° C. in 10 ml of physiological saline and the rate of release of the vardenafil from the drug formulation in 900 ml of physiological saline within the first 5 minutes in the USP pedal stirrer apparatus at 50 rotations per minute at 37° C. is at least 70%.

16. The drug formulation according to claim 8 or 12, comprising from 40% to 99% sugar alcohol of the total formulation.

17. A drug formulation in the form of an uncoated tablet which disintegrates rapidly in the mouth and releases vardenafil hydrochloride trihydrate in the mouth without swallowing the tablet, said tablet comprising
vardenafil hydrochloride trihydrate;
sorbitol; and
mannitol; and
wherein:
said vardenafil hydrochloride trihydrate is in micronized form with a mean particle size of less than 20 μm;
said vardenafil hydrochloride trihydrate comprises from 0.8% to 25% of the formulation, calculated as vardenafil free base; and
said sorbitol and mannitol together comprises from 40% to 99% of the formulation.

18. The drug formulation of claim 4, wherein said sugar alcohol is a mixture of mannitol and sorbitol.

* * * * *